United States Patent
Miyake (10) Patent No.: US 9,833,375 B2
(45) Date of Patent: Dec. 5, 2017

(54) WALKING SUPPORT APPARATUS AND WALKING SUPPORT METHOD

(71) Applicants: Tokyo Institute of Technology, Meguro-ku, Tokyo (JP); KIKUCHI SEISAKUSHO CO., LTD., Hachioji-shi, Tokyo (JP)

(72) Inventor: Yoshihiro Miyake, Tokyo (JP)

(73) Assignee: TOKYO INSTITUTE OF TECHNOLOGY, Meguro-Ku, Tokyo (JP)

(*) Notice: Subject to any disclaimer, the term of this patent is extended or adjusted under 35 U.S.C. 154(b) by 0 days.

(21) Appl. No.: 14/758,332

(22) PCT Filed: Dec. 25, 2013

(86) PCT No.: PCT/JP2013/007588
§ 371 (c)(1),
(2) Date: Jun. 29, 2015

(87) PCT Pub. No.: WO2014/103305
PCT Pub. Date: Jul. 3, 2014

(65) Prior Publication Data
US 2016/0000635 A1    Jan. 7, 2016

(30) Foreign Application Priority Data

Dec. 28, 2012  (JP) .................. 2012-288597

(51) Int. Cl.
*A63B 24/00*   (2006.01)
*A61H 3/00*    (2006.01)
(Continued)

(52) U.S. Cl.
CPC ................ *A61H 3/00* (2013.01); *A61B 5/112* (2013.01); *A61B 5/4836* (2013.01);
(Continued)

(58) Field of Classification Search
CPC ... A61B 5/04888; A61B 5/112; A61B 5/1122; A61B 5/4836; A61B 5/6823; A61H 3/00;
(Continued)

(56) References Cited

U.S. PATENT DOCUMENTS 6,064,912 A * 5/2000 Kenney ................. A61F 5/0111
                                                                    602/16
7,367,958 B2 * 5/2008 McBean ............ A61B 5/04888
                                                                    602/16
(Continued)

FOREIGN PATENT DOCUMENTS

GB       2444679 A     6/2008
JP    2004208976 A     7/2004
(Continued)

OTHER PUBLICATIONS

International Preliminary Report on Patentability corresponding to Application No. PCT/JP2013/007588; dated Jan. 28, 2015, with English translation.
(Continued)

*Primary Examiner* — Glenn Richman
(74) *Attorney, Agent, or Firm* — Cantor Colburn LLP (57) ABSTRACT

A walking support apparatus supports the walking movement of a walking person. The walking person may be an elderly person, a disabled person, an invalid, an athlete, a learner, or the like. A measurement unit measures walking information with respect to the walking person, and generates data that represents the walking information. An attachment applies an action to the arm of the walking person according to the walking information data measured by the measurement unit. Such an arrangement provides improved walking movement via the effect on the arm movement when the walking person is walking.

14 Claims, 7 Drawing Sheets

(51) Int. Cl.
  *A61H 1/02* (2006.01)
  *A61B 5/11* (2006.01)
  *A61B 5/00* (2006.01)

(52) U.S. Cl.
  CPC ......... *A61H 1/0274* (2013.01); *A61H 1/0277* (2013.01); *A61H 1/0281* (2013.01); *A61B 5/1122* (2013.01); *A61B 5/6823* (2013.01); *A61H 2001/0211* (2013.01); *A61H 2003/007* (2013.01); *A61H 2201/1207* (2013.01); *A61H 2201/165* (2013.01); *A61H 2201/5007* (2013.01); *A61H 2201/5061* (2013.01); *A61H 2201/5064* (2013.01); *A61H 2201/5069* (2013.01); *A61H 2201/5079* (2013.01); *A61H 2201/5084* (2013.01)

(58) Field of Classification Search
  CPC .. A61H 1/0274; A61H 1/0277; A61H 1/0281; A61H 2201/1207; A61H 2201/5007; A61H 2201/5061; A61H 2201/5069; A61H 2201/5079; A61H 2201/5084; A61H 2201/5064; A61H 2201/165; A61H 5/112; A61H 5/1122; A61H 5/4836; A61H 5/6823; A61H 2003/007; A61F 5/0111; A61F 5/01
  See application file for complete search history.

(56) References Cited

U.S. PATENT DOCUMENTS

| | | | | |
|---|---|---|---|---|
| 9,339,431 | B2* | 5/2016 | Menard | ................ A61H 3/04 |
| 2009/0227925 | A1* | 9/2009 | McBean | .............. A61F 5/0127 |
| | | | | 602/16 |
| 2009/0276058 | A1* | 11/2009 | Ueda | .................... A61H 1/0274 |
| | | | | 623/57 |
| 2010/0041959 | A1 | 2/2010 | Iwata et al. | |
| 2011/0166488 | A1 | 7/2011 | Miyake | |
| 2013/0131560 | A1* | 5/2013 | Ferguson | ................ A61H 3/00 |
| | | | | 601/33 |
| 2015/0173993 | A1* | 6/2015 | Walsh | ..................... A61H 3/00 |
| | | | | 414/4 |

FOREIGN PATENT DOCUMENTS

| | | |
|---|---|---|
| JP | 2005227909 A | 8/2005 |
| JP | 2006503658 A | 2/2006 |
| JP | 2006102156 A | 4/2006 |
| JP | 2007029113 A | 2/2007 |
| JP | 2007061260 A | 3/2007 |
| JP | 2010264320 A | 11/2010 |
| JP | 2011177278 A | 9/2011 |
| JP | 2012105732 A | 6/2012 |
| WO | 2004037344 A1 | 5/2004 |

OTHER PUBLICATIONS

International Search Report corresponding to Application No. PCT/JP2013/007588; dated Apr. 8, 2014, with English translation.
Written Opinion of the International Searching Authority corresponding to Application No. PCT/JP2013/007588; dated Apr. 8, 2014, with English translation.
Japanese Notification of Reason(s) for Refusal corresponding to Application 2012-288597; dated Aug. 30, 2016, with partial English translation.
Supplementary European Search Report corresponding to Application No. 13869550.7; dated Sep. 22, 2016.

* cited by examiner

WALKING SUPPORT APPARATUS AND WALKING SUPPORT METHOD

CROSS-REFERENCE TO RELATED APPLICATIONS

This is the U.S. national stage of application No. PCT/JP2013/007588, filed Dec. 25, 2013. Priority under 35 U.S.C. §119(a) and 35 U.S.C. §365(b) is claimed from Japanese Application No. 2012-288597, filed Dec. 28, 2012, the disclosure of which is also incorporated herein by reference.

FIELD OF THE INVENTION

The present invention relates to a technique for supporting and improving walking movement of a human being.

DESCRIPTION OF THE RELATED ART

In order to support the walking movement of an elderly person, disabled person, or an invalid with physical difficulties with respect to walking movement, or in order to provide such a person with improvement due to rehabilitation, a walking support apparatus is employed. As a conventional method for supporting walking or providing improvement, a method is known in which walking movement is directly supported. Specifically, a method has been proposed in which walking movement is directly and dynamically supported by means of a prosthetic limb, a power assist robot (actuator), or the like. As another method for supporting walking or providing walking with improvement, a method has also been proposed in which a walking rhythm is measured, and a walking person is rhythmically stimulated in synchronization with the walking rhythm thus measured in order to indirectly support the walking movement of the person. Japanese Patent Applications Laid Open No. 2010-264320, No. 2006-102156, No. 2005-227909 disclose the related art.

However, with such a method in which the walking movement is directly supported, an external force is dynamically applied to the leg so as to promote the walking movement. Thus, in the event of trouble, such an arrangement leads to the person falling, which is a safety problem. Also, with such a method, the leg of such a walking person having physical difficulties or a problem with respect to walking movement is forcibly moved. Thus, in some cases, such an arrangement inflicts suffering on the walking person. Also, if the person becomes accustomed to the walking support by means of such a walking support apparatus, in some cases, this leads to degeneration of the motor ability of the leg, leading to a risk of the patient being unable to walk without such a walking support apparatus, which is a problem from the viewpoint of learning effects.

SUMMARY OF THE INVENTION

The present invention has been made in view of such a situation. Accordingly, it is an exemplary purpose of an embodiment of the present invention to provide a walking support apparatus which is capable of providing improvement to at least one of the aforementioned problems in the conventional walking support methods.

An embodiment of the present invention relates to a walking support apparatus. The walking support apparatus comprises: a measurement unit that measures walking information with respect to a walking person; and an attachment that applies an action to at least one arm of the walking person according to the walking information measured by the measurement unit.

The present inventor has recognized that, in walking movement, there is a close relation between the leg movement and the arm movement via mediation by the brain. Instead of directly affecting the leg movement, by affecting the arm movement which has a relationship with the brain, such an embodiment is capable of providing improved walking movement from within the person via the arm movement. Thus, such an arrangement provides at least one from among improved safety, reduced suffering of the walking person, suppressing degradation of the ability to exercise, and learning effects, as compared with an arrangement configured to directly affect the leg movement.

The "walking information" represents information with respect to walking, which may include (i) information that represents a trajectory of a portion such as the arm, leg, chest, lumbar region, abdominal region, neck, head, center of gravity of the body, or the like, (ii) information that represents the orientation when the person is walking, and (iii) the arm swinging frequency, leg movement frequency, and information that relates to the walking rhythm such as the phase relation between the arm swinging and the leg movement. In the present specification, the "arm" represents a region from the shoulder up to the fingertips.

Also, the attachment may be configured to adjust the bend angle of at least one elbow joint of the walking person according to the measurement result obtained by the measurement unit. Also, the attachment may be configured to limit the range of movement of the at least one elbow joint of the walking person according to the measurement result obtained by the measurement unit.

By changing the bend angle of the elbow joint, such an arrangement is capable of changing the moment of inertia of the arm, thereby controlling the orientation of the walking movement.

Also, the attachment may be configured to adjust the angle of at least one shoulder joint of the walking person according to the measurement result obtained by the measurement unit. Also, the attachment may be configured to limit the range of movement of the at least one shoulder joint of the walking person according to the measurement result obtained by the measurement unit.

Also, the attachment may be configured to control the bend angle of the at least one elbow joint in synchronization with the walking movement. Also, the attachment may be configured to control the bend angle of the at least one shoulder joint in synchronization with the walking movement.

Also, the measurement unit may comprise a sensor to be attached to a lumbar region or otherwise an abdominal region of the walking person. Also, the walking information may include a trajectory of the lumbar region or the abdominal region.

Also, the attachment may be adjusted such that the trajectory shows left-right symmetry.

It should be noted that any combination of the aforementioned components may be made, and any component of the present invention or any manifestation thereof may be mutually substituted between a method, apparatus, and so forth, which are effective as an embodiment of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

BRIEF DESCRIPTION OF THE DRAWINGS

FIGS. 4A and 4B are diagrams each showing a swinging trajectory of the lumbar region, and specifically, FIG. 4A shows a state in which there is no limit on the movement of the person using the attachment, and FIG. 4B shows a state in which only the movement of the right elbow is limited by means of the attachment;

FIGS. 5A and 5B are diagrams each showing a swinging trajectory of the lumbar region, and specifically, FIG. 5A shows a state in which there is no limit on the movement of the person using an attachment, and FIG. 5B shows a state in which the movement of both elbows are limited by means of the attachments;

DETAILED DESCRIPTION OF THE INVENTION

Description will be made below regarding preferred embodiments according to the present invention with reference to the drawings. The same or similar components, members, and processes are denoted by the same reference numerals, and redundant description thereof will be omitted as appropriate. The embodiments have been described for exemplary purposes only, and are by no means intended to restrict the present invention. Also, it is not necessarily essential for the present invention that all the features or a combination thereof be provided as described in the embodiments.

Figure 1:
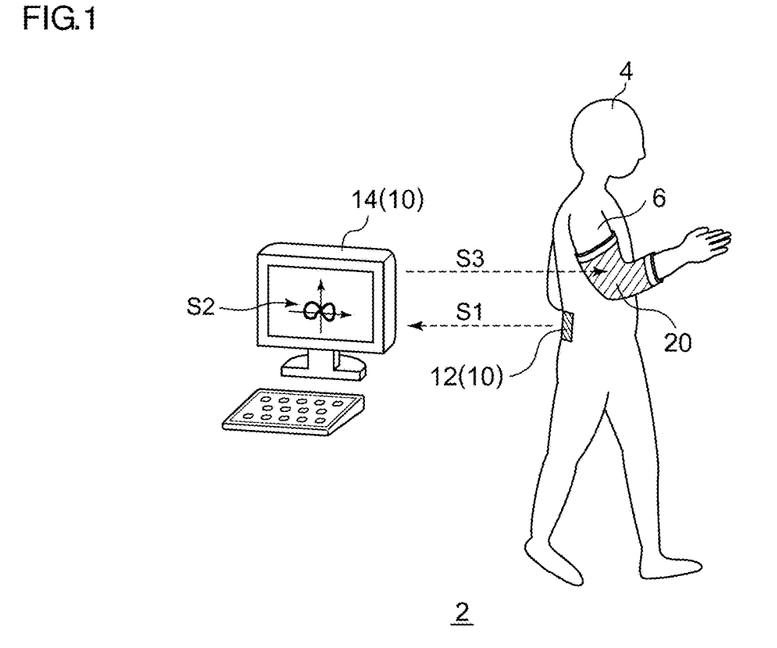
FIG. 1 is a diagram showing a walking support apparatus according to an embodiment.

FIG. 1 is a diagram showing a walking support apparatus 2 according to an embodiment. The walking support apparatus 2 supports the walking of a walking person (subject) 4. The walking support apparatus 2 is designed for a walking person 4 having difficulties with respect to desired walking, examples of which include elderly persons, disabled persons, and invalids.

The walking support apparatus 2 mainly includes a measurement unit 10 and an attachment 20. A walking evaluation system described in Japanese Patent Applications Laid Open No. 2010-264320 may be employed as the measurement unit 10, for example. The measurement unit 10 includes an acceleration sensor 12 and a computer (which will also be referred to as the "control unit") 14. The acceleration sensor 12 is attached to the lumbar region or otherwise the abdominal region of the walking person 4. The acceleration sensor 12 outputs data S1 which indicates the accelerations in the left-right direction (x-axis direction), the vertical direction (y-axis direction), and the traveling direction (front-back direction, z-axis direction). The computer 14 performs signal processing on the data S1 received from the acceleration sensor 12 so as to generate data S2 (which will be referred to as "walking information data" hereafter) which represents walking information. In the present embodiment, the walking information data S2 is configured as data that indicates a three-dimensional trajectory of the movement of the lumbar region or otherwise the abdominal region of the walking person 4.

Figure 2:
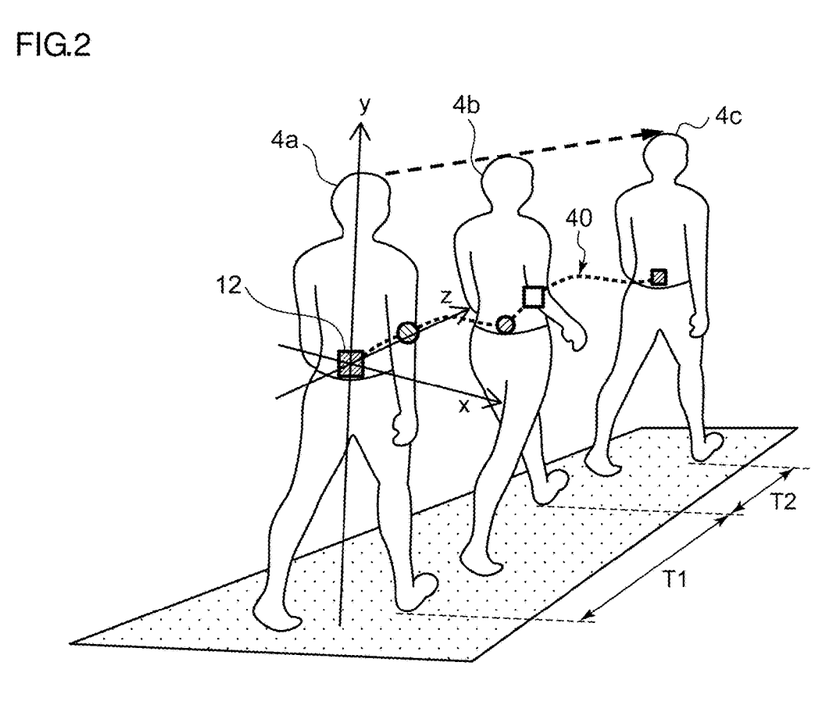
FIG. 2 is a diagram showing a trajectory of the lumber region of a walking subject measured by a measurement unit.

FIG. 2 is a diagram showing a trajectory of the lumbar region of the walking person 4 measured by the measurement unit 10. In FIG. 2, the image 4a represents a state in which the heel of the right foot makes contact with the ground. The image 4b represents a next state in which the heel of the left foot makes contact with the ground. The image 4c represents a next state in which the heel of the right foot makes contact with the ground. The walking movement of a human being can be regarded as a cycle of a first period T1 (4a to 4b) from a stage in which the heel of the right foot makes contact with the ground up to a stage in which the heel of the left foot makes contact with the ground, and a second period T2 (4b to 4c) from a stage in which the heel of the left foot makes contact with the ground up to a stage in which the heel of the right foot makes contact with the ground.

For example, the measurement unit 10 may acquire, as the walking information data S2, a trajectory (which will be referred to as "swinging trajectory" hereafter) obtained by projecting the movement of the lumbar region shown in FIG. 2 onto an XY plane. Also, an XYZ three-dimensional trajectory may be acquired as the walking information data S2. Also, a four-dimensional trajectory including a time-axis component may be acquired as the walking information data S2. Also, a three-dimensional trajectory comprising coordinate data obtained by projecting the movement onto an XY plane and the time-axis component may be acquired as the walking information data S2.

Returning to FIG. 1, the computer 14 generates control information S3 to be used to control the attachment 20 such that the swinging trajectory of the lumbar region or otherwise the abdominal region of the walking person 4 approaches a trajectory (which will be referred to as the "target trajectory") configured as an ideal trajectory that would be detected in an ideal walking movement. The control information S3 may include information that determines whether the attachment 20 is to be attached to the right arm or the left arm, information that determines the kind of action to be applied to the arm, information that determines the level of the action to be applied to the arm, information that determined when the action is to be applied to the arm, and the like.

The attachment 20 is attached to the arm 6 of the walking person 4 so as to apply an action to the arm 6 of the walking person 4 according to the measurement result obtained by the measurement unit 10. As an investigation result obtained by the present inventor, it has been found that the movement of the arm is tightly linked to the walking movement. Thus, when an action is applied to the arm movement, this has an effect not only on the movement of the arm receiving the action, but also on the overall walking movement. Thus, the attachment 20 may preferably be configured to have an effect on the walking information, and more specifically, on the data S1 measured by the measurement unit 10. That is to say, the kind of action to be applied to the arm 6 is not restricted in particular.

The arm 6 represents a region from the shoulder up to the fingertips. Specific examples of "an action applied to the arm 6" include an action applied to at least one arm joint, i.e., any one of a shoulder joint, an elbow joint, a wrist joint, or a finger joint, and a desired combination of these. Examples of an action applied to such a joint include: controlling the bend angle of the joint such that it becomes a predetermined value; setting a limit on the movable joint angle such that the walking person 4 can move the joint in a predetermined range; a resistance (load) applied to the joint movement; and the like.

Figure 3A:
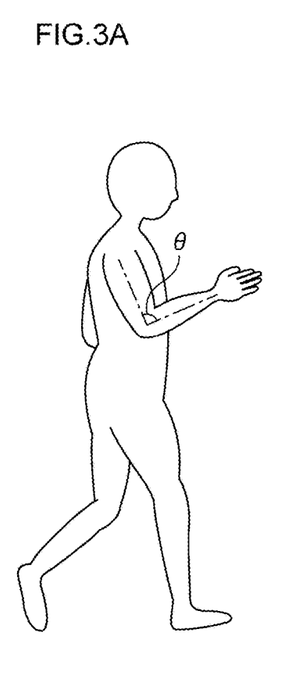
FIGS. 3A and 3B are diagrams each showing an attachment.
Figure 3B:
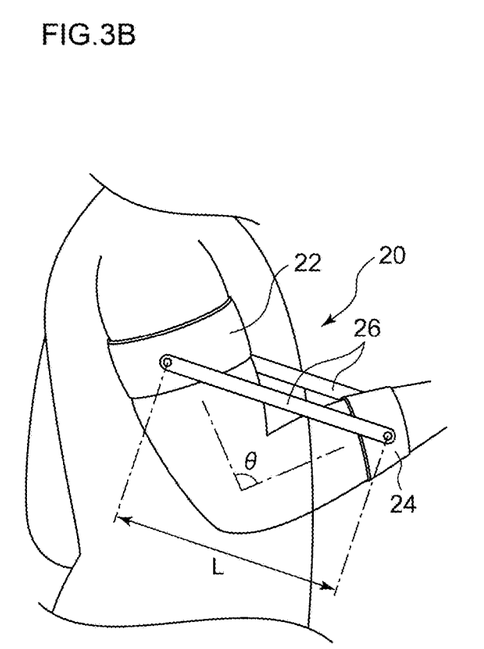

In the present embodiment, the attachment 20 applies an action to the elbow joint of the walking person 4. FIGS. 3A and 3B are diagrams each showing the attachment 20. In the present embodiment, the attachment 20 is configured to have an effect on the bend angle θ of the elbow joint.

For example, the attachment 20 may include a first portion 22 to be fixedly attached to the upper arm, a second portion 24 to be fixedly attached to the lower arm, and an adjuster member 26 configured to adjust the distance L between the first portion 22 and the second portion 24. The adjuster member 26 may be configured employing an electric actuator. Also, the adjuster member 26 may be configured to automatically control the bend angle θ according to the control information S3 generated by the computer 14.

Alternatively, the adjuster member 26 may be configured such that its length L can be adjusted manually. In this case, the bend angle θ may be adjusted manually by the walking person 4 himself/herself or otherwise by a helper based on the control information S3 generated by the computer 14.

It should be noted that the specific configuration of the attachment 20 is not restricted in particular. Rather, the attachment 20 may preferably be configured to allow the bend angle θ of the elbow joint to be adjusted.

Also, such an attachment 20 may be attached to only the right arm, only the left arm, or both arms of the walking person 4 as necessary, and specifically, based on the control information S3 generated by the computer 14. In a case in which such an attachment 20 is attached to both arms, there may be a difference between the elbow joint adjustment angles θl and θr.

The above is the configuration of the walking support apparatus 2 according to the embodiment.

The present inventor performed the following experiments in order to confirm the effectiveness of the walking support apparatus 2.

In the experiment, with a healthy person as the subject to be investigated, the swinging trajectory of the lumbar region of the subject was measured for each of a state in which no attachment 20 was attached to the subject such that there was no limit on the movement of the subject, a state in which the attachment 20 was attached to only the right elbow so as to limit the movement of the right elbow, and a state in which such an attachment 20 was attached to both elbows so as to limit the movement of both elbows.

Figure 4A:
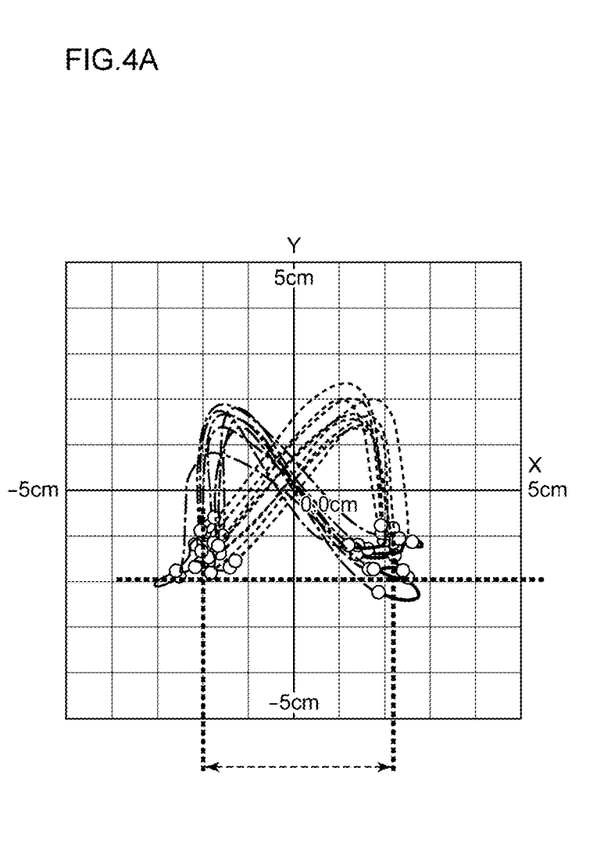
Figure 4B:
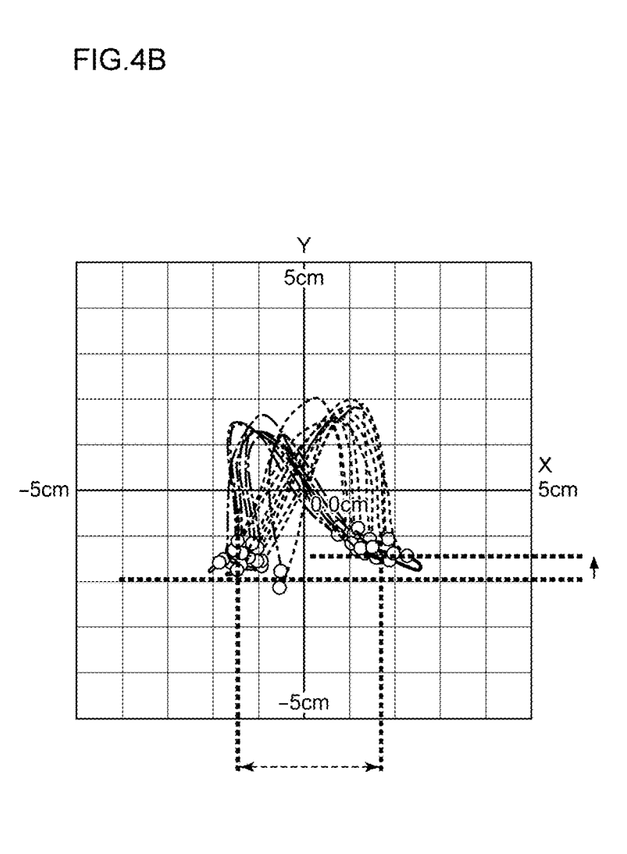

FIGS. 4A and 4B are diagrams respectively showing a swinging trajectory of the lumbar region in a state in which no attachment 20 is attached to the subject such that there is no limit on the movement of the subject, and a swinging trajectory of the lumbar region in a state in which the attachment 20 is attached to only the right elbow so as to limit the movement of the right elbow. Each circular symbol shown together with the trajectory represents the coordinate point of the lumbar region at a time point when the subject touches down on the ground.

As a comparison result obtained by comparing the trajectories shown in FIGS. 4A and 4B, it has been found that, in a case in which the angle θr of the right elbow is fixed, this reduces the amplitude in the left-right direction, and the lowest points (at a point when the right foot touches down on the ground) have an increased height. Thus, it has been found that this leads to left-right asymmetry in the walking movement.

Figure 5A:
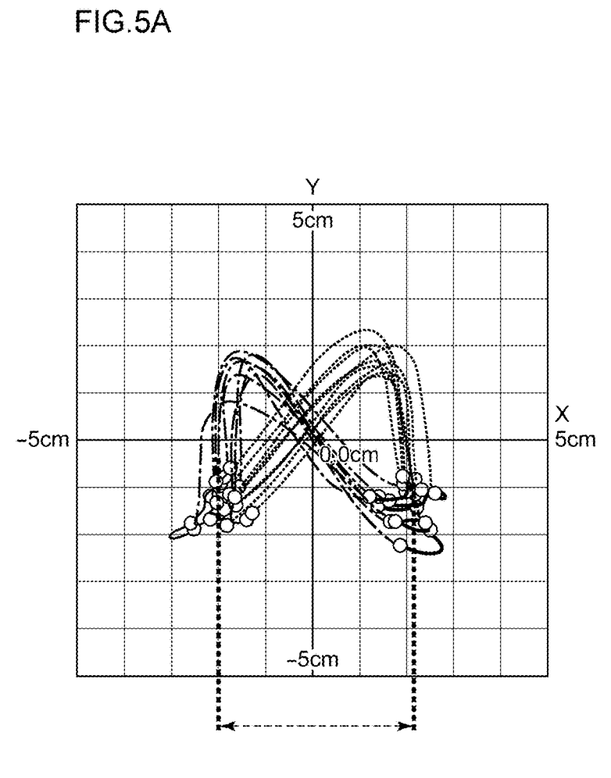
Figure 5B:
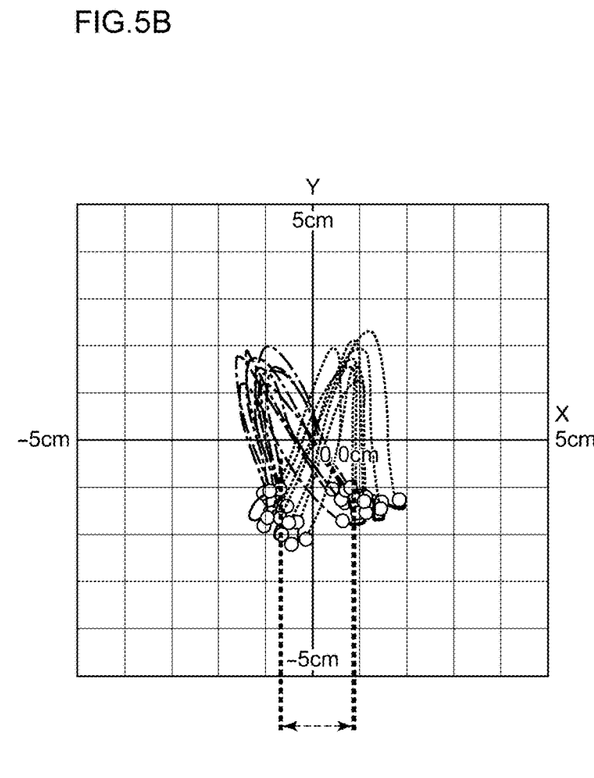

FIGS. 5A and 5B are diagrams respectively showing a swinging trajectory of the lumbar region in a state in which no attachment 20 is attached to the subject such that there is no limit on the movement of the subject, and a swinging trajectory of the lumbar region in a state in which such an attachment 20 is attached to both elbows such that the movement of both elbows is limited by means of the attachments 20. As a comparison result obtained by comparing the trajectories shown in FIGS. 5A and 5B, it has been found that, in a case in which the bend angles θl and θr of the respective elbows are each fixed, this further reduces the amplitude in the left-right direction, as compared with that in a case in which only the right elbow is fixed as shown in FIG. 4B.

As described above, it has been found that, by limiting the movement of the elbow, and by selecting, from the left elbow or right elbow, the elbow to be subjected to limitation of movement, such an arrangement is capable of providing an effect on the walking movement, thereby allowing the trajectory of the lumbar region to be changed.

Figure 6A:
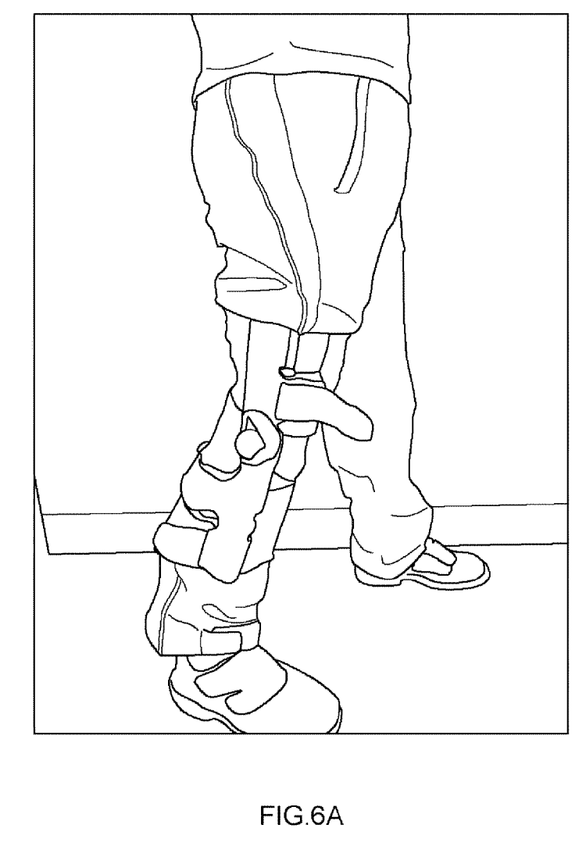
FIG. 6A is a diagram showing a state in which the right knee joint of the subject is fixed by means of an attachment.
Figure 6B:
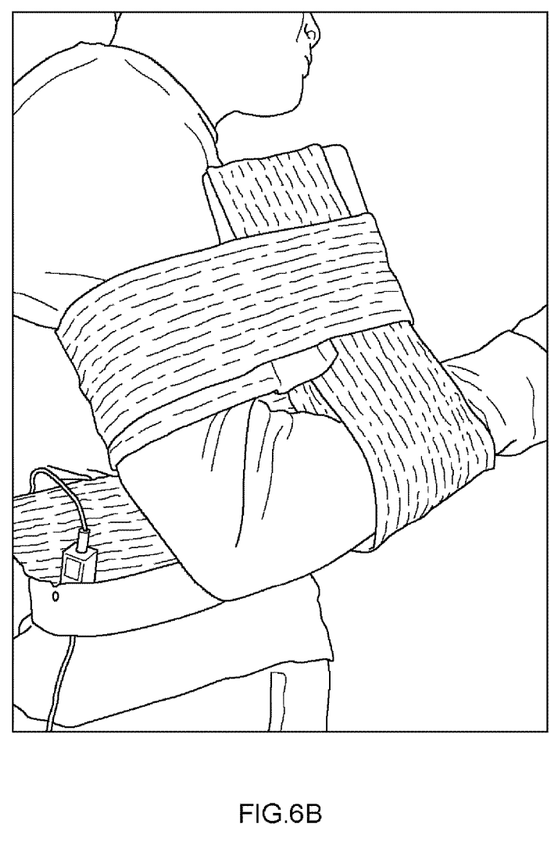
FIG. 6B is a diagram showing a state in which the right elbow joint of the subject is fixed by means of an attachment.

In the next experiment, in order to confirm the effectiveness of the walking support apparatus 2, the angle of the right knee of a subject (a healthy person) was fixed so as to provide a pseudo-hemiplegic gait. FIG. 6A is a diagram showing a state in which the right knee joint is fixed, and FIG. 6B is a diagram showing a state in which the right knee joint is fixed by means of the attachment 20. The elbow joint is fixed at a bend angle θ of approximately 90 degrees.

Figure 7A:
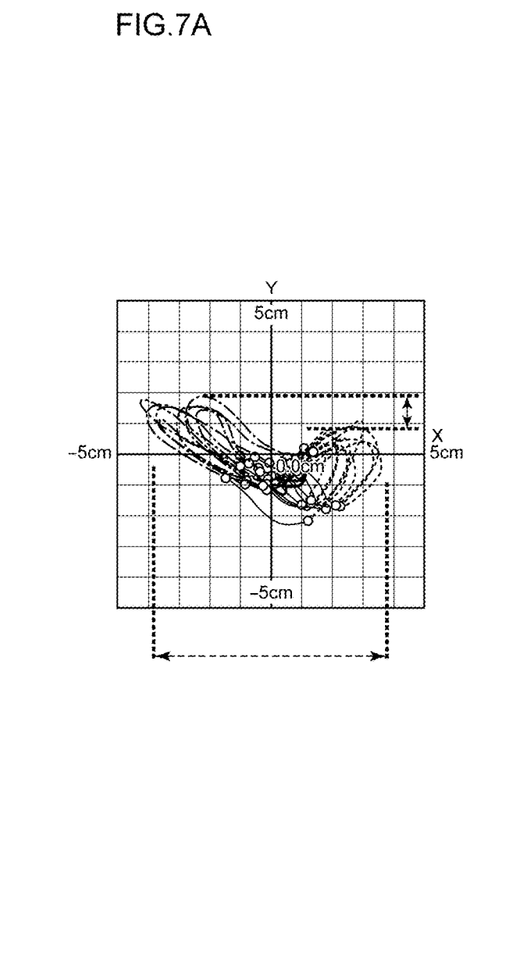
FIGS. 7A through 7C are diagrams each showing improved walking movement provided by means of the walking support apparatus in a case of simulating a pseudo-hemiplegic gait.
Figure 7B:
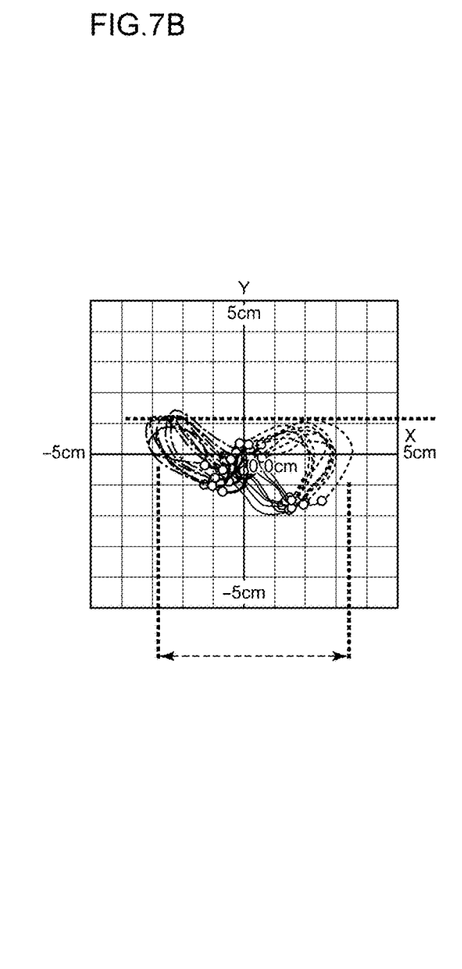
Figure 7C:
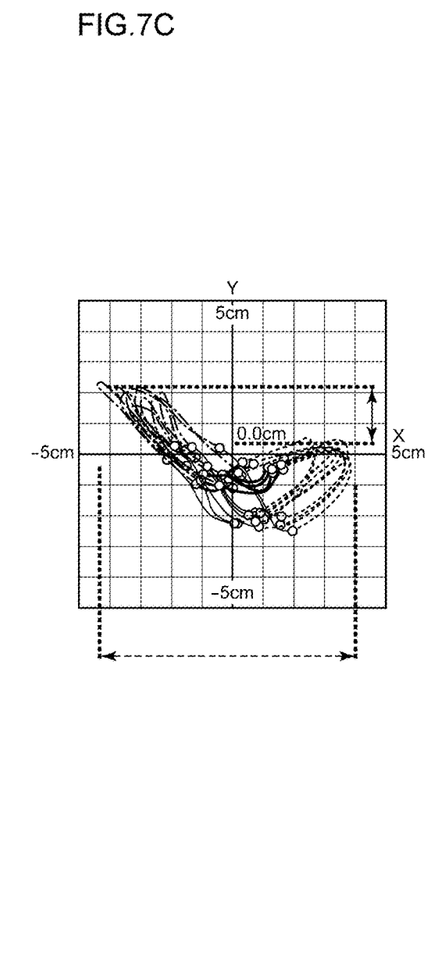

FIGS. 7A through 7C are diagrams each showing improvement in such a pseudo-hemiplegic gait provided by means of the walking support apparatus 2. In general, the swinging trajectory preferably has left-right symmetry. Thus, the attachment 20 may preferably be adjusted such that the trajectory has left-right symmetry.

FIG. 7A shows a state in which there is no limit on the movement of both elbows of the subject, FIG. 7B shows a state in which the movement of the right elbow is limited, and FIG. 7C shows a state in which the movement of the left elbow is limited.

As shown in FIG. 7A, in a case in which a hemiplegic gait is simulated, the swinging trajectory of the lumbar region shows asymmetry in the left-right direction. Specifically, the highest points on the left side are higher than those on the right side, and the amplitude on the left side is larger than that on the right side. Furthermore, the amplitude in the vertical direction and the amplitude in the left-right direction are larger than those shown in FIG. 5A obtained from a healthy person.

As shown in FIG. 7B, it has been found that, by limiting the movement of the right-side elbow on the same side as a paralyzed leg, such an arrangement provides a reduced difference between the coordinate point of the left-side highest point and the coordinate point of the right-side highest point, thereby providing the waist with reduced swinging in the vertical direction. At the same time, such an arrangement provides reduced amplitude in the left-right direction, thereby providing the waist with reduced swinging in the left-right direction. The cause of such an improvement is considered to be as follows. That is to say, by limiting the movement of the right elbow, the moment of inertia of the right arm is changed. This increases the frequency of the right arm movement, leading to an increased frequency of the walking rhythm on the right side.

This promotes the movement of the right leg, thereby providing improved symmetry in the left-right direction.

Conversely, in a case of limiting the movement of the left-side elbow on the opposite side of a paralyzed leg as shown in FIG. 7C, such an arrangement provides an increased difference between the coordinate point of the left-side highest point and the coordinate point of the right-side highest point, thereby providing the waist with increased swinging in the vertical direction. At the same time, such an arrangement provides increased amplitude in the left-right direction, thereby providing the waist with increased swinging in the left-right direction. The cause of such degradation is considered to be as follows. That is to say, by limiting the movement of the left elbow, the moment of inertia of the left arm is changed. This increases the frequency of the left arm movement, leading to an increased frequency of the walking rhythm on the left side. This leads to a further increased difference in the walking rhythm between the left side and the right side on which the walking rhythm has a low frequency due to the paralyzed right leg. This results in degraded symmetry in the left-right direction.

As described above, with the walking support apparatus 2 according to the embodiment, an experimental result has been obtained in which such an arrangement was capable of providing improvement in the walking of a subject in a case of simulating a pseudo-hemiplegic gait.

Next, description will be made regarding the operation of the walking support apparatus 2 in a case of supporting the walking of an actual elderly person, a disabled person, or the like.

The measurement unit 10 monitors the walking state, i.e., the trajectory. The computer 14 may generate the control information S3 by means of a feedback control operation such that the trajectory thus monitored matches its target trajectory, so as to control the attachment 20. Alternatively, the computer 14 may study beforehand the relationship between the state of the attachment 20 and the effect of the attachment 20 on the trajectory, and may generate the control information S3 using an open loop control method, so as to control the attachment 20.

Thus, such an arrangement is capable of providing improvement in the walking of a patient with actual paralysis, a disabled person, and an elderly person, in the same way as with the pseudo-paralyzed subject.

In summary, with conventional walking support techniques, such an arrangement is designed so as to directly affect the walking movement of the person in order to provide improved walking. In contrast, the walking support apparatus 2 according to the embodiment has an effect on the arm movement of the person, which relates to walking via mediation by the brain, thereby providing the person with improved walking movement from within the person himself/herself. Thus, such an arrangement provides at least one from among improved safety, reduced suffering of the walking person, suppressing degradation of the ability to exercise, and learning effects.

The moment of inertia of the arm changes according to the bend angle θ of the elbow joint. Thus, by optimizing the bend angle θ of the elbow joint, such an arrangement is capable of adjusting the trajectory in a more flexible manner. This allows the trajectory to approach its target trajectory.

Description has been made regarding the present invention with reference to the embodiment. The above-described embodiment has been described for exemplary purposes only, and is by no means intended to be interpreted restrictively. Rather, it can be readily conceived by those skilled in this art that various modifications may be made by making various combinations of the aforementioned components or processes, which are also encompassed in the technical scope of the present invention. Description will be made below regarding such modifications.

Modification 1

In the embodiment, the attachment 20 is set to a fixed state during the walking movement of the person. In contrast, in the modification 1, the attachment 20 may be configured to control the bend angle θ of the elbow joint in synchronization with the walking movement of the person. This allows the moment of inertia of the arm, i.e., the frequency of the swinging of the arm, to be dynamically adjusted for each cycle in synchronization with the walking movement. This allows the walking information with respect to the walking person 4 to approach the target walking information.

Modification 2

Description has been made in the embodiment regarding an arrangement in which the attachment 20 controls the angle of the elbow joint. However, the present invention is not restricted to such an arrangement. In the modification 2, the attachment 20 may control any one of the elbow joint, shoulder joint, wrist joint, finger joint, or a desired combination of these. In addition to the state of the elbow joint, the state of other kinds of joints also has an effect on walking movement. In this case, a joint that differs from the elbow joint may be adjusted in synchronization with the walking movement.

Modification 3

Also, in addition to providing an effect on the arm movement by means of the attachment 20, audible, visual, or tactile rhythmical stimulation may be applied to the walking person in synchronization with his/her walking movement. Such an arrangement more effectively provides the walking person 4 with improved walking movement.

Modification 4

Description has been made in the embodiment regarding an arrangement in which the measurement unit 10 is controlled such that the trajectory on the XY plane measured by the measurement unit 10 matches its target trajectory. However, the present invention is not restricted to such an arrangement.

For example, in the first stage for improving the walking movement, such an arrangement may monitor only the X coordinate component (i.e., movement in the left-right direction) or otherwise only the Y coordinate component (i.e., movement in the vertical direction), and the attachment 20 may be controlled such that the X coordinate (or otherwise Y coordinate) component of the trajectory thus measured matches its target trajectory. Also, only a part (e.g., a right half, a left half, an upper side, a lower side, or a slanting part) of the trajectory may be monitored, and the attachment 20 may be controlled such that the part of the trajectory thus monitored matches its target trajectory.

Also, only the Z coordinate component (front-back direction) of the trajectory may be monitored, and the attachment 20 may be controlled such that the Z coordinate component of the trajectory thus monitored matches its target trajectory.

Also, the attachment 20 may be controlled such that the X-direction speed or Y-direction speed matches its target value, or such that both match their target values, in addition to the trajectory on the XY plane. Also, the attachment 20 may be controlled such that the X-direction acceleration or Y-direction acceleration matches its target value, or such that both match their target values, in addition to the trajectory on the XY plane.

Description has been made in the embodiment regarding an arrangement in which the trajectory on the XY plane is monitored. Also, the attachment 20 may be controlled such that the three-dimensional trajectory in the XYZ space matches its target trajectory. Also, the attachment 20 may be controlled such that the four-dimensional trajectory including the time-axis component matches its target trajectory.

Modification 5

Description has been made in the embodiment regarding an arrangement in which the walking information is measured using the acceleration sensor 12. However, the present invention is not restricted to such an arrangement. Also, a gyro sensor or a speed sensor may be employed instead of the acceleration sensor 12. Also, as used in three-dimensional modeling, the walking information data S2 may be generated by means of a combination of a marker and a camera. Also, the walking movement of the walking person 4 may be recorded by means of multiple cameras, and the walking information data S2 may be generated by means of image processing. Also, a pressure sensor may be attached to each of the soles of the feet of the person, or otherwise, pressure sensors may be arranged on the floor, so as to measure (i) walking rhythm, (ii) pressure distribution on the soles of the feet, load on the soles of the feet, load shift on the soles of the feet, (iii) stride, or the like, so as to generate the walking information data S2.

Modification 6

Description has been made in the embodiment regarding an arrangement in which only the movement of the lumbar region is monitored. Also, other kinds of portions such as the head, jaw, neck, shoulder, upper arm, elbow, lower arm, thigh, knee, heel, ankle, etc., may be measured so as to acquire the walking information data S2.

Modification 7

Description has been made in the embodiment regarding an arrangement configured to provide improved walking movement to an elderly person, disabled person, or invalid. However, the present invention is not restricted to such an arrangement. The walking support apparatus 2 may be applied to a fashion model, an ordinary person, or an athlete who desires to correct his/her walking form. That is to say, the walking support apparatus 2 is applicable to correcting the walking form of a healthy person. Also, the walking support apparatus 2 may be used for the transmission of traditional performing arts such as dancing or the like which involve walking movement.

Description has been made regarding the present invention with reference to the embodiments using specific terms. However, the above-described embodiments show only the mechanisms and applications of the present invention for exemplary purposes only, and are by no means intended to be interpreted restrictively. Rather, various modifications and various changes in the layout can be made without departing from the spirit and scope of the present invention defined in appended claims.

The invention claimed is:

1. A walking support apparatus comprising:
   a measurement unit structured to measure walking information with respect to a walking person;
   an attachment structured to be attached to at least one arm of the walking person, and to apply an action to said at least one arm of the walking person; and
   a control unit structured to control the attachment according to the walking information measured by the measurement unit,
   wherein the walking support apparatus is structured to support walking without directly applying an action to a leg of the walking person.

2. The walking support apparatus according to claim 1, wherein the attachment is configured to adjust a state of at least one elbow joint of the walking person according to a measurement result obtained by the measurement unit.

3. The walking support apparatus according to claim 2, wherein the attachment is configured to adjust an angle of the at least one elbow joint of the walking person, and/or to limit a range of movement of the at least one elbow joint, according to the measurement result obtained by the measurement unit.

4. The walking support apparatus according to claim 3, wherein the attachment is configured to control a bend angle of the at least one elbow joint in synchronization with the walking movement.

5. The walking support apparatus according to claim 1, wherein the attachment is configured to change a state of at least one shoulder joint of the walking person according to a measurement result obtained by the measurement unit.

6. The walking support apparatus according to claim 5, wherein the attachment is configured to adjust an angle of the at least one shoulder joint of the walking person, and/or to limit a range of movement of the at least one shoulder joint, according to the measurement result obtained by the measurement unit.

7. The walking support apparatus according to claim 6, wherein the attachment is configured to control a bend angle of the at least one shoulder joint in synchronization with the walking movement.

8. The walking support apparatus according to claim 1, wherein the measurement unit comprises a sensor to be attached to a lumbar region or otherwise an abdominal region of the walking person,
   and wherein the walking information includes a trajectory of the lumbar region or the abdominal region.

9. The walking support apparatus according to claim 1, wherein the attachment is configured to affect the at least one arm of the walking person in synchronization with the walking movement.

10. The walking support apparatus according to claim 1, wherein the controller is structured to generate a control information that determines that determines when the action is to be applied to the at least one arm of the walking person.

11. The walking support apparatus according to claim 1, wherein the controller is structured to generate a control information that determines a level of the action to be applied to the at least one arm of the walking person.

12. The walking support apparatus according to claim 1, wherein the action includes applying a resistance against a joint movement of the at least one arm of the walking person.

13. The walking support apparatus according to claim 1, wherein the action is applied so as to change a frequency of a swinging of the at least one arm of the walking person.

14. A walking support method comprising:
measuring walking information with respect to a walking person;
attaching an attachment to at least one arm of the walking person; and
controlling the attachment according to the walking information thus measured,
wherein walking is supported without directly applying an action to a leg of the walking person.

* * * * *